United States Patent
Privitera et al.

(10) Patent No.: US 10,085,812 B2
(45) Date of Patent: Oct. 2, 2018

(54) SURGICAL INSTRUMENT WITH SEPARATE TOOL HEAD AND METHOD OF USE

(71) Applicant: AtriCure, Inc., Mason, OH (US)

(72) Inventors: Salvatore Privitera, Mason, OH (US); Matthew J. Winkler, Liberty Township, OH (US)

(73) Assignee: AtriCure, Inc., Mason, OH (US)

( * ) Notice: Subject to any disclaimer, the term of this patent is extended or adjusted under 35 U.S.C. 154(b) by 0 days.

(21) Appl. No.: 15/207,893

(22) Filed: Jul. 12, 2016

(65) Prior Publication Data

US 2016/0317235 A1 Nov. 3, 2016

Related U.S. Application Data

(63) Continuation of application No. 13/422,208, filed on Mar. 16, 2012, now Pat. No. 9,408,659, which is a continuation of application No. 12/061,319, filed on Apr. 2, 2008, now abandoned.

(60) Provisional application No. 60/909,666, filed on Apr. 2, 2007.

(51) Int. Cl.
| | |
|---|---|
| *A61B 17/10* | (2006.01) |
| *A61B 34/00* | (2016.01) |
| *A61B 18/14* | (2006.01) |
| *A61B 17/32* | (2006.01) |
| *A61B 17/00* | (2006.01) |
| *A61B 34/30* | (2016.01) |
| *A61B 18/00* | (2006.01) |

(52) U.S. Cl.
CPC .............. *A61B 34/70* (2016.02); *A61B 17/10* (2013.01); *A61B 17/32* (2013.01); *A61B 18/1442* (2013.01); *A61B 18/1445* (2013.01); *A61B 18/1447* (2013.01); *A61B 34/30* (2016.02); *A61B 2017/00243* (2013.01); *A61B 2017/320044* (2013.01); *A61B 2018/00577* (2013.01); *A61B 2018/145* (2013.01); *A61B 2034/305* (2016.02)

(58) Field of Classification Search
CPC .. A61B 2017/00243; A61B 2019/2234; A61B 18/1447
See application file for complete search history.

(56) References Cited

U.S. PATENT DOCUMENTS

| | | | | |
|---|---|---|---|---|
| 5,715,832 | A * | 2/1998 | Koblish | ................. A61B 10/06 600/564 |
| 7,591,818 | B2 * | 9/2009 | Bertolero | ................. A61B 1/12 606/51 |
| 2005/0256522 | A1 * | 11/2005 | Francischelli | ..... A61B 18/1442 606/41 |
| 2006/0047278 | A1 * | 3/2006 | Christian | ........... A61B 18/1442 606/41 |

* cited by examiner

*Primary Examiner* — Kathleen Holwerda
*Assistant Examiner* — Christina Lauer
(74) *Attorney, Agent, or Firm* — Dorton + Willis, LLP; Ryan Willis

(57) ABSTRACT

Surgical instruments are disclosed in which an elongated shaft is used in conjunction with a separate, remotely actuable tool head for performing a procedure on a target tissue. The shaft has a tool engagement member carried at its distal end that is remotely actuable through the shaft to engage and release the tool head.

8 Claims, 4 Drawing Sheets

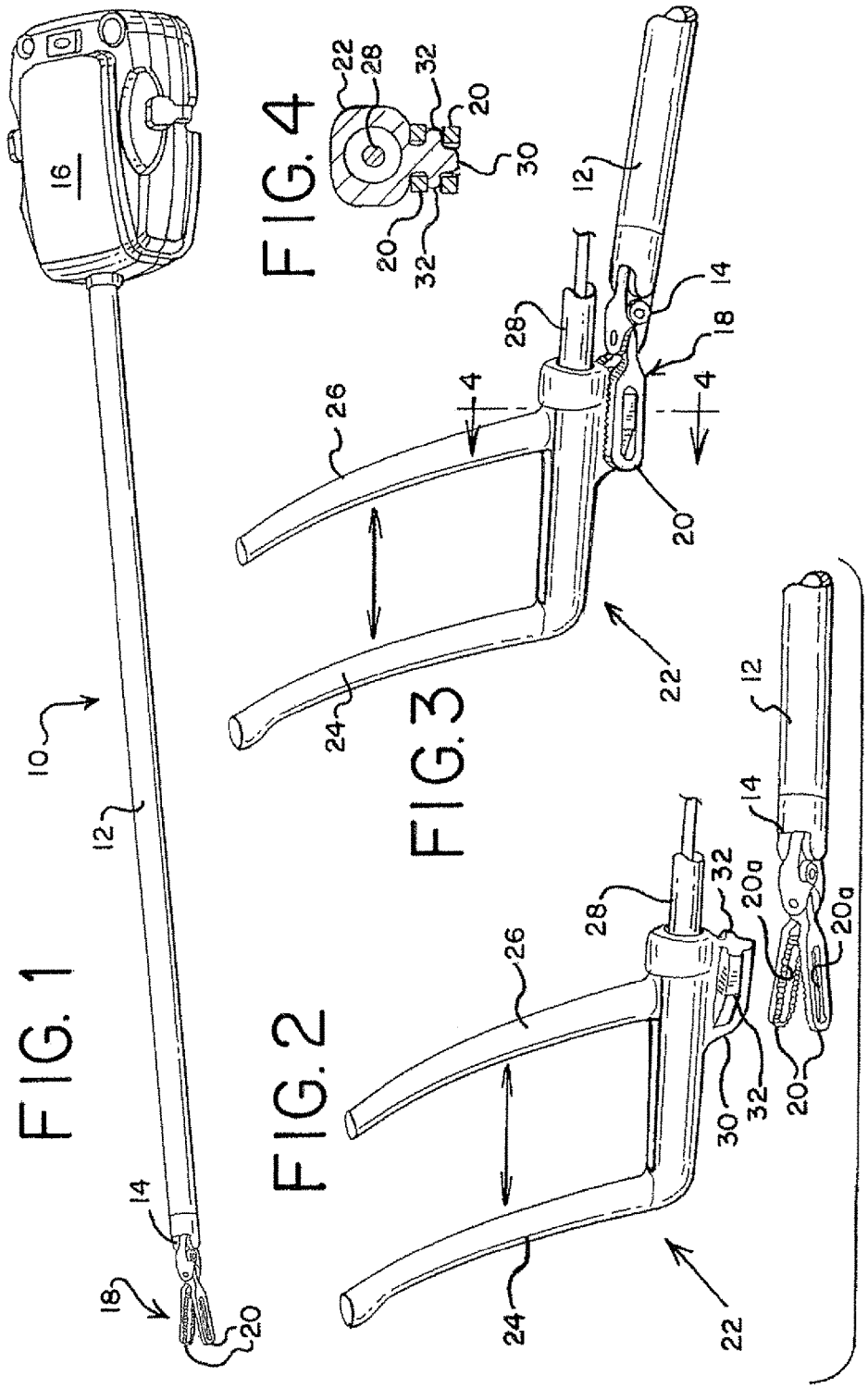

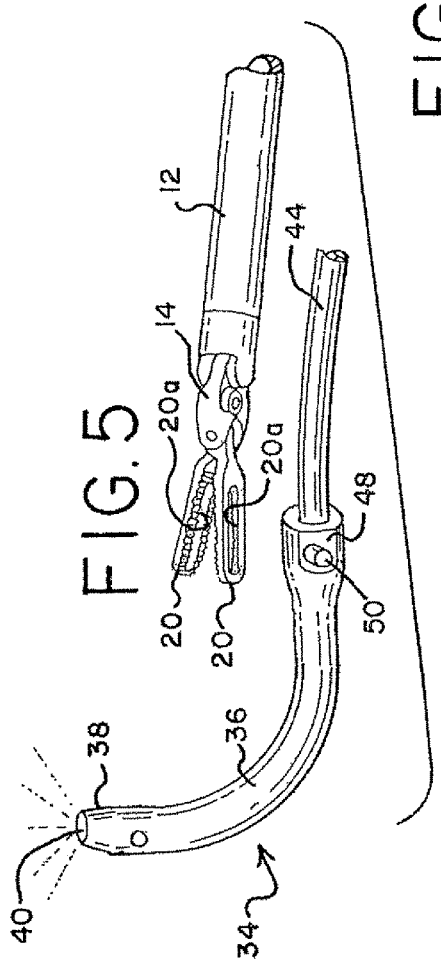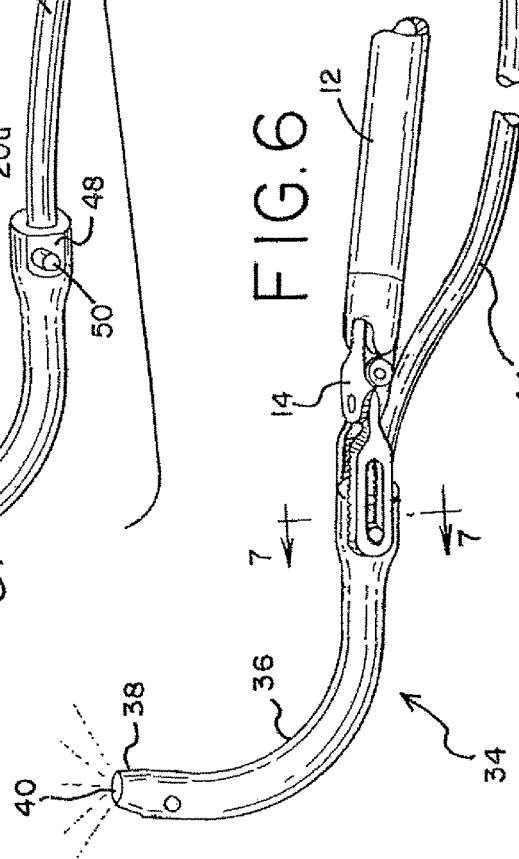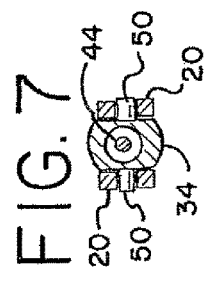

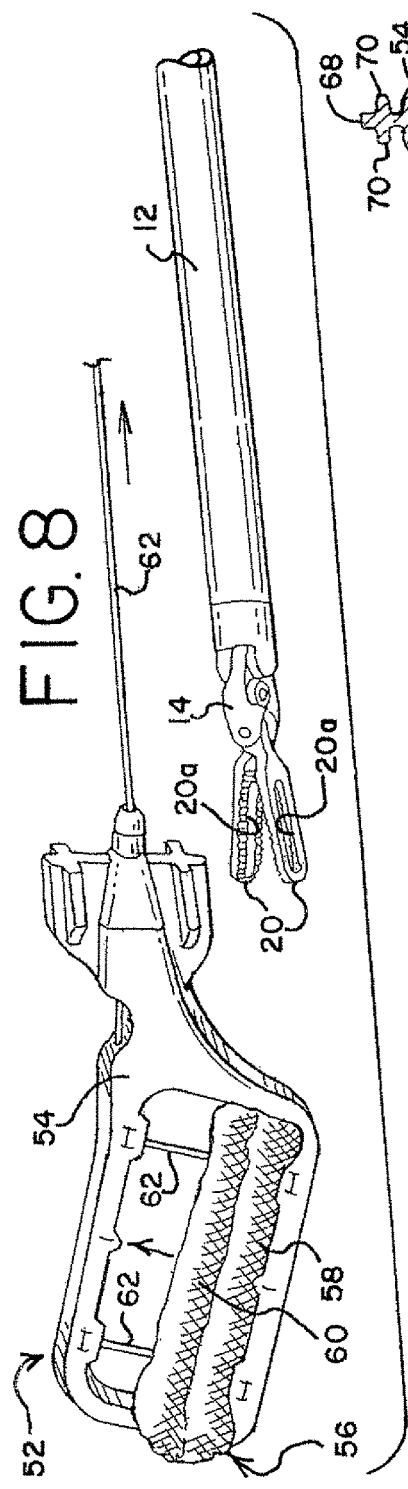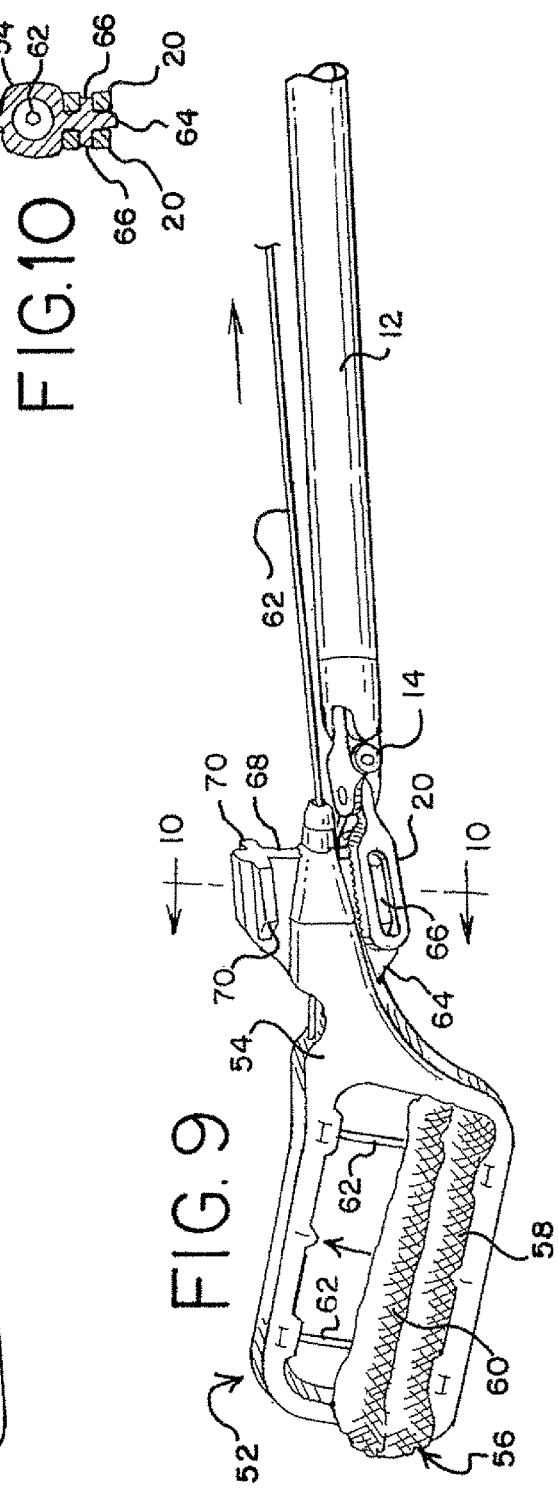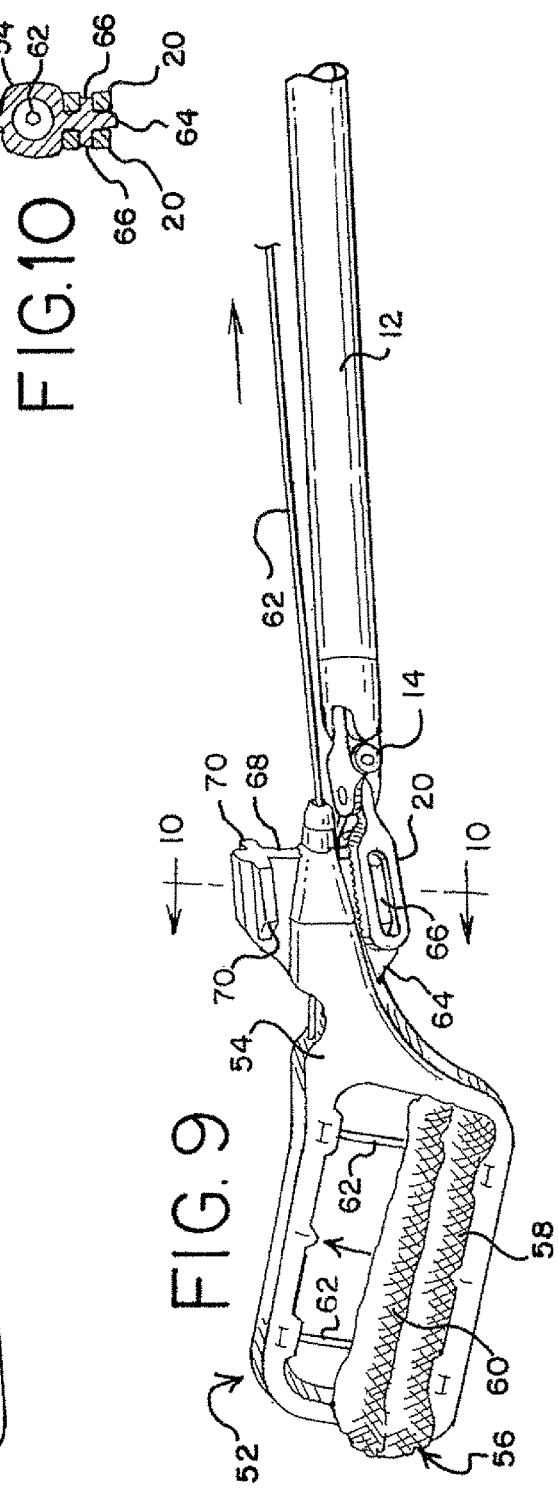

SURGICAL INSTRUMENT WITH SEPARATE TOOL HEAD AND METHOD OF USE

CROSS REFERENCE TO RELATED APPLICATION

This application claims the benefit of U.S. Provisional Patent Application Ser. No. 60/909,666, filed Apr. 2, 2007, which is incorporated herein by reference.

BACKGROUND

The present application is related to surgical instruments and, more specifically but not exclusively, to robotic surgery instruments and methods for their use. Specifically, the present application relates to the provision of a plurality of specially configured tool heads for use with a control arm, which may be a robotic arm of a robotic surgical instrument, having an elongated shaft and preferably an articulatable "wrist" or articulation joint located at its distal or working end.

The tool heads disclosed and described herein are particularly, but not exclusively, suited for use in cardiac ablation procedures for the treatment of atrial fibrillation using electro-surgical RF energy, or some other energy, as shown and described for example in U.S. Pat. No. 6,546,935, which is incorporated herein by reference.

During the performance of cardiac ablation procedures, various instruments may be used to create transmural lines of ablation in tissue, such as an ablation clamp having opposed jaw members having opposed electrodes thereon, an ablation "pen" and a surgical dissector. Such instruments are shown generally in U.S. Pat. No. 7,113,831 and U.S. Published Application 2006/0084974 (showing an ablation clamp with opposed jaw members), U.S. Published Applications 2006/0161147 and 2006/0161149 (both showing an ablation pen), and U.S. Published Application 2005/0203561 (showing a lighted dissector), all of which are incorporated herein by reference. In another procedure, a clip may be applied externally to the left atrial appendage (LAA) to reduce the risks of clot generation associated with the LAA. Such a clip and clip applicator are shown in U.S. application Ser. No. 12/033,935, filed Feb. 20, 2008, which is also incorporated herein by reference. Each of the aforementioned devices or tools is typically carried on its own dedicated hand piece and a shaft, with the operating head at the distal end thereof.

SUMMARY

By way of the present application, tools for performing cardiac ablation and other procedures are provided as discrete interchangeable independent devices or tool heads that are intended to be used with a control arm, such as a robotic arm or a durable, e.g., reusable, arm. The tool heads are provided with a tether connected directly thereto to provide for actuation of the tool head. (As used herein, "actuation" or "actuable" are broadly understood to mean energizing or controlling the tool head mechanically, hydraulically, pneumatically, thermally, or activating a light/laser/light pipe/fiber optic, or providing a vacuum/suctionor fluid delivery and the like, as well as combinations thereof.) Specifically, each of the tool heads may include at least one gripping or clamping surface designed to be carried by the jaws of a forceps or grasper mounted to the distal end of the shaft of the control arm. The tool head may be removably mounted to the control arm in any of a variety of ways described below, or by other mounting arrangements.

The actuation and/or energizing means for generating movement is preferably connected to the tool head separate from the control arm in a manner that permits remote actuation/energization of the tool head, (i.e. external to the body) independent of the control arm after the tool heads have been introduced, for example, by minimally invasive means, to a surgical site interior of the body.

Because the tool head is completely independent from the control arms, the tool head may be passed from one control arm to another control arm, or exchanged between control arms, and the various tools may be selectively grasped by the control arm to permit instrument exchanges during procedures. The tool heads may be introduced either through the same access port as the control arm or through a separate access port, into the surgical site. Thus, in a procedure, all of the tool heads needed for the procedure may be separately introduced into proximity of the surgical site, such as into a cavity at the start of the procedure and be readily available for use in connection with one or more control arms.

In one embodiment, the tool heads are provided with an extending or fin-like surface for gripping by jaws of a control arm. Preferably, the fins are made of a material having some compressibility, which allows the jaws of control arm forceps to better grip and hold the tool head.

Additionally, or alternatively, the fin and the forceps may be formed with complementarily-shaped interfitting surfaces that mate when the tool is gripped by the forceps. Such surfaces may be shaped to provide selected alignment of the tool with respect to the forceps. In one embodiment, for example, the jaws of the forceps of the control arm have an open or relieved interior or apertures or fenestrations and the gripping surfaces of the tool heads may be formed with one or more complementarily-shaped protrusion that is received within the fenestration interior of the jaws.

In a further alternative, these surfaces may be reversed, and the gripping or clamping surface may comprise a pocket or aperture that receives the closed jaws or projecting surfaces thereof and may be grasped by moving the jaws toward their open position.

As another option, the tool heads may be formed with two or more gripping surfaces, which permits a tool head to be simultaneously held by two or more control arms so that the tool head can be passed from a first control arm to a second control arm, and allows for both control arms to work in unison.

BRIEF DESCRIPTION OF THE DRAWINGS

FIG. 1 is a perspective view of a control arm having an articulatable wrist and a grasper at its distal end.

FIG. 2 is a perspective view of the distal end of the control arm of FIG. 1 and a tool head in the form of an ablation clamp in accordance with the present disclosure.

FIG. 3 is a perspective view similar to FIG. 3 in which the tool head is held by the control arm.

FIG. 4 is a cross-sectional view taken along line 4-4 of FIG. 3.

FIG. 5 is a perspective view of the distal end of the control arm of FIG. 1 and a tool head in the form of a blunt dissector in accordance with the present disclosure.

FIG. 6 is a perspective view similar to FIG. 5 in which the tool head is held by the control arm.

FIG. 7 is a cross-sectional view taken along line 7-7 of FIG. 6.

FIG. 8 is a perspective view of the distal end of the control arm of FIG. 1 and a tool head in the form of a clip applicator in accordance with the present disclosure.

FIG. 9 is a perspective view similar to FIG. 8 in which the tool head is held by the robotic arm.

FIG. 10 is a cross-sectional view taken along line 10-10 of FIG. 9.

DETAILED DESCRIPTION

Figure 11:
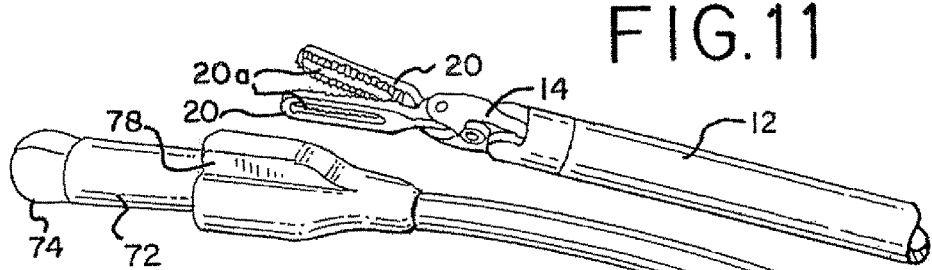
FIG. 11 is a perspective view of the distal end of the control arm of FIG. 1 and a tool head in the form of an ablation pen in accordance with the present disclosure.

With reference to FIG. 1, there is seen one form of a control arm with which the surgical instruments disclosed herein are adapted to be used. The illustrated control arm is a robotic arm 10 comprising a component of a telesurgical system (not shown), such as the daVinci Surgical System, available from Intuitive Surgical, Inc. of Mountain View, Calif., shown in U.S. Pat. No. 6,770,081, which is incorporated herein by reference. Alternatively, the control arm is not necessarily a robotic arm or associated with a robotic surgical system, although that is one system in which this subject matter has particular application. For example, the control arm may simply be a standard surgical grasping tool such as those available from Fehling Surgical Instrument, Inc., of Acworth, Ga., or graspers of the type disclosed in U.S. Pat. No. 5,728,121, which is incorporated herein by reference.

The illustrated robotic arm 10 includes an elongated shaft 12 and a wrist-like articulation mechanism 14 at its distal end. A housing 16 at the proximal end of the assembly 10 couples the assembly to the telesurgical system. The housing 16 contains the mechanism for controlling (e.g., rotating) the shaft 12, articulating the wrist 14, and actuating a forceps 18 mounted to the wrist mechanism 14 carried on the distal end of the shaft 12. The illustrated forceps 18 is known as a cardiere forceps in which the jaws 20 are fenestrated, or otherwise have an opening or relief in their gripping surface. Preferably, and as shown, the gripping surfaces of the jaws are serrated.

With reference to FIGS. 2-4, there is seen a tool head 22 comprising an clamp having opposed jaws 24, 26 for use with the robotic arm assembly 10 shown in FIG. 1. The illustrated clamping jaws 24, 26 may preferably be as shown and described in U.S. Pat. No. 7,113,831 and U.S. Published Application 2006/0084974. Each jaw 24, 26 includes an elongated electrode (not shown) that is adapted to receive bipolar RF energy for creating transmural ablation lines in tissue held between the jaws 24, 26. Jaw 24 may be stationary, while jaw 26 may be moveable toward and away from jaw 26, with the mating surfaces of the jaws 24, 26 remaining substantially parallel. The electrical and mechanical connections 28 for activating the electrodes carried on the jaws and for opening and closing the jaws are connected to the tool head 22 separate and independent from the control arm, such as shaft 12 of the robotic tool 10.

Because the activation sources for the tool head are separate from the control arm, the tool head may be exchanged between different control arms, the tool head may be released from the control arm and a different tool head attached, and multiple tool heads may be preselected and placed in or near the surgical site for user convenience. This feature has particular benefit in a minimally invasive surgery in that, for example, the tool heads expected to be needed for a selected surgery may be inserted in to the body cavity, creating what may be referred to as a tool kit or tool chest within the body cavity, and the surgeon or robotic instrument may use a single control arm for grasping and using each tool head, as needed, without the need for repeatedly removing the control to exchange or replace tools as needed. Further, the tool heads may be for one-time use only and disposable, with the control arm, and any associated articulation control mechanism, being reusable, if so desired.

To facilitate the grasping of the individual tool head 22 by the grasper 18, the tool head 22 may be provided, in one embodiment, with a clamping surface 30. Specifically, the illustrated clamp carries a generally flat or fin-like protrusion on the side of the tool opposite the jaw members 24, 26, although other configurations for the clamping surface or other arrangements other than a clamping surface are also contemplated. In order to enhance the grip of the jaws on the clamping surface, the fin 30 has opposed protrusions 32 sized and shaped to fit into the fenestrations 20a on the jaws 20 of the forceps 18. As shown, the protrusions 32 are formed on both surfaces of the clamping surface, although a protrusion could be formed on only one of the clamping surfaces. Also, if the fenestration 20a and protrusion 32 are complementarily shaped, such as one concave and the other convex, and non-circular, gripping of the tool head 22 in a particular orientation to the jaws 20 is facilitated.

As noted above, it is contemplated that other tools or tool heads useful in performing cardiac ablation or other intended procedures could similarly be provided with a clamping or gripping surface or other grasping arrangement. Turning to FIGS. 5-7, a tool head 34 in the form of a blunt dissector is shown in combination with the working end of a control arm such as a robotic shaft. The illustrated dissector 34 may preferably be as shown and described in U.S. Published Application 2005/0203561. The dissector comprises an arcuate section 36 with a smooth outer surface and a generally circular cross-sectional shape. However, the geometry may vary depending on the targeted anatomy. The arcuate section 36 has a blunt and rounded distal end 38. As illustrated, the distal end of the dissector 35 includes a light source 40 that emits visible energy. The light source 40 is powered by a battery carried in housing 42 that is connected to the dissector 35 by an insulated conductor/tether 44 such that the battery remains external to the body during a procedure. The battery housing 42 includes a switch 46 for activating the light source 40. To facilitate the grasping of the dissector 34 by the jaws 20 of the forceps 18, the dissector 35 includes a clamping surface 48 at its proximal end having at least one and preferably opposed posts 50 adapted to be received in the fenestrations 20a of the opposed jaws 20.

FIGS. 8-10 show the working end of the robotic shaft in combination with tool head 52 comprising a clip applicator for applying an occlusion clamp or clip to the tissue to be closed, which may include the left atrial appendage, or other vessel or tissue. The clip applicator and clip may be as shown and described in pending U.S. patent application Ser. No. 12/033,935, filed Feb. 20, 2008. The tool head comprises a frame 54 with an open interior with a fabric covered clip 56 preloaded therein. The clip 56 comprises two legs 58, 60 that are spread apart a distance sufficient to allow it to be placed over target tissue, e.g., the left appendage of the heart. To this end control sutures, wires or strings 62 are attached to leg 60 of the clip such that retraction of the sutures 62 spreads the legs 58, 60. The proximal end of the sutures 62 remain external to the body for remote actuation. For cooperation with a control arm, the clip applicator 52 includes a clamping surface 64 with elongated protrusions 66 similar to that shown in conjunction with the ablation clamp 22 described above. In addition, the clip applicator 52 is provided with a second clamping surface 68 similar to clamping surface 64 and having elongated protrusions 70. The second clamping surface permits the tool head 52 to be grasped simultaneously by two robotic arm assemblies 10, thus permitting the tool head to be passed from one robotic arm to a second robotic arm. This feature is not limited to a clip applicator, and as such, each of the tool heads described herein may also include a second clamping surface.

Figure 12:
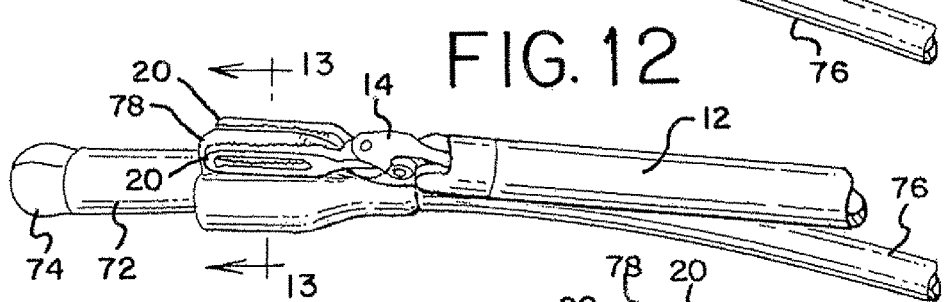
FIG. 12 is a perspective view similar to FIG. 11 in which the tool head is held by the control arm.
Figure 13:
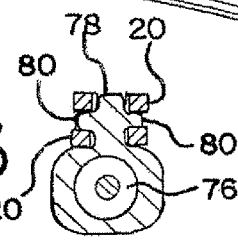
FIG. 13 is a cross-sectional view taken along line 13-13 of FIG. 12.

FIGS. 11-13 show an ablation pen 72 in combination with the distal end of the control arm of a robotic surgical instrument. The ablation pen 72 may preferably be as shown and described in U.S. Published Applications 2006/0161147 and 2006/0161149. The ablation pen 72 includes a head 74 carrying two electrodes (not shown) capable of being energized with bi-polar RF energy. An insulated electrical conductor 76 is provided (as a tether) for transmitting energy to the electrodes.

Similar to the examples described above, the pen 72 is provided with a clamping surface 78 adapted to be held between the jaws 20 of the forceps 18. As seen in FIG. 11, the clamping surface 78 does not include the complementarily-shaped protrusions associated with the clamping surfaces of the previously disclosed embodiments. Instead, the clamping surface 78 is made from or provided with a covering of a compressible material that is more readily deformable under the closing force achieved by the jaws 20, thus permitting the jaws 20 to more firmly grip the clamping surface 78. This is shown in FIG. 13, where it can be seen that the clamping surface 78 has been deformed such that a portion 80 thereof resides in the fenestrations of the jaws 20. As can be appreciated, the clamping surface of the tool head may be both deformable and have complementarily-shaped protrusions to enhance gripping by a forceps. Other friction-enhancing materials or surfaces may be used to enhance grasping by the control arm.

Figure 14:
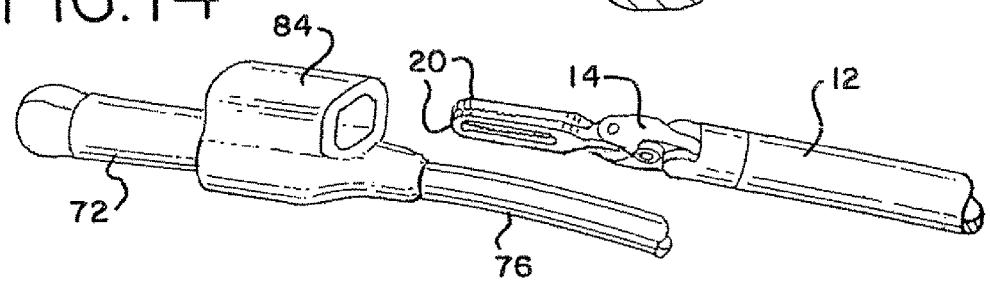
FIG. 14 is a perspective view similar to FIG. 11 except that it has an alternative clamping surface.
Figure 15:
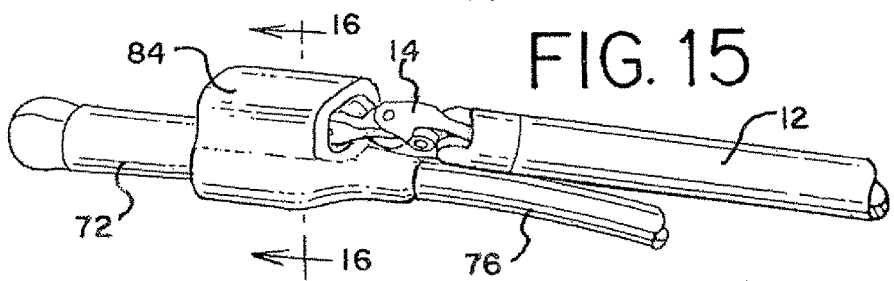
FIG. 15 is a perspective view similar to FIG. 14 in which the tool head is held by the control arm.
Figure 16:
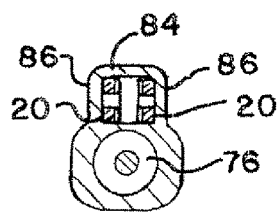
FIG. 16 is a cross-sectional view taken along line 16-16 of FIG. 15.

While each of the tool heads described thus far has had a clamping surface adapted to be held between the closed jaws of a forceps, other configurations for securing the tool head are contemplated. For example, and with reference to FIGS. 14-16, the tool head 72 (shown for illustrative purposes in the form of an ablation pen as in FIGS. 11-13) is provided by a receptacle 84, which may also be referred to as a clamping surface, that is adapted to be held by the spread-apart or open jaws of the forceps. Specifically, the clamping surface 84 is in the form of a pocket or sleeve with an open interior sized to receive the closed jaws 20 of the forceps 8. The pocket or sleeve 84 has opposed side walls 86 that are engaged by the outer surface of the jaws 20 (best seen in FIG. 16). Of course, as described in connection with the outer embodiments, the interior of the sleeve may be provided with protrusions sized to be received in the fenestrations of the jaws and/or a deformable or enhanced friction surface.

While the surgical instruments have been described in terms of those particularly appropriate for cardiac applications, this is not by way of limitation, but for illustration. Indeed, any surgical instruments adapted for use with robotic devices may advantageously include the clamping surface described above.

What is claimed:

1. A tool head, devoid of an elongated shaft and a handle, for performing a medical ablation procedure for use in combination with a surgical device having a shaft and a grasping device on the distal end of the shaft, the tool head comprising a grasping fin for engagement by the grasping device and a tether extending from the tool head and disengaged from the surgical device that may be used to reposition an ablation clamp of the tool head and supply electrical power to the tool head, the ablation clamp comprising a first clamping jaw having a first ablation electrode, and a second clamping jaw having a second ablation electrode, where the tether is in electrical communication with the first and second ablation electrodes, where the tether is operatively coupled to at least one of the first clamping jaw and the second clamping jaw in order to reposition the first and second clamping jaws with respect to one another among an open position where the first and second clamping jaws having a first spacing between one another, and a clamping position having a second spacing that is less than the first spacing.

2. The tool head of claim 1 wherein:
the first and second ablation electrodes of the first and second jaws are located on respective clamping surfaces;
each respective clamping surface has at least one of a protrusion or relieved area shaped to engage the other of a protrusion or a relieved area on the other jaw.

3. The tool head of claim 2 wherein each respective clamping surface has opposed protrusions or relieved areas shaped to engage complementary protrusions or relieved areas of the other jaw.

4. The tool head of claim 2 wherein each respective clamping surface is compressible.

5. The tool head of claim 1 wherein:
the grasping device includes opposed repositionable graspers; and,
the opposed repositionable graspers are interposed by at least a portion of the grasping fin when the grasping device engages the tool head.

6. A method for performing a medical ablation procedure in an in vivo surgical field comprising:
introducing into the in vivo surgical field a radio frequency (RF) ablation clamp tool head, devoid of an elongated shaft and a handle, for ablating tissue;
introducing into the in vivo surgical field a first robotic arm uncoupled to the RF ablation clamp tool head;
repositioning the first robotic arm to couple the first robotic arm to the RF ablation clamp tool head post introducing the first robotic arm to the in vivo surgical field;
repositioning a first jaw of the RF ablation clamp tool head with respect to a second jaw of the RF ablation clamp tool head to clamp tissue therebetween while the first robotic arm engages the RF ablation clamp tool head;
ablating the tissue by energizing at least one electrode associated with at least one of the first jaw and the second jaw.

7. A tool head, devoid of an elongated shaft and a handle, for performing a medical ablation procedure for use in combination with a surgical device having a grasping device, the tool head comprising a grasping fin for engagement by the grasping device and a tether extending from the tool head and disengaged from the surgical device that may be used to reposition an ablation clamp of the tool head, the ablation clamp comprising a first stationary jaw having a first ablation electrode, a second repositionable jaw having a second ablation electrode, and a housing statically fixed to the first stationary jaw, where the housing defines a track along which the second repositionable jaw is repositioned to provide parallel closure of the second repositionable jaw with respect to the first stationary jaw, and where the tether is operatively coupled to the second repositionable jaw in order to reposition the second repositionable jaw with respect to the first stationary jaw, and where the tether is in electrical communication with the first and second ablation electrodes.

8. A method for performing a medical procedure in an in vivo surgical field comprising:
- introducing into the in vivo surgical field a tool head with a tether, the tool head devoid of an elongated shaft and a handle, as part of performing the medical procedure;
- introducing into the in vivo surgical field a first robotic arm uncoupled to the tool head and the tether;
- repositioning the first robotic arm to couple the first robotic arm to the tool head post introducing the first robotic arm into the in vivo surgical field;
- repositioning a first portion of the tool head with respect to a second portion of the tool head, using the tether, to clamp tissue between the first and second portions of the tool head while the first robotic arm engages the tool head.

* * * * *